United States Patent [19]

Brown et al.

[11] E Patent Number: Re. 33,221

[45] Reissued Date of Patent: May 22, 1990

[54] DENTAL RESTORATIVE CEMENT PASTES

[75] Inventors: Walter E. Brown, Rockville; Laurence C. Chow, Potomac, both of Md.

[73] Assignee: American Dental Association Health Foundation, Washington, D.C.

[21] Appl. No.: 51,739

[22] Filed: May 18, 1987

Related U.S. Patent Documents

Reissue of:

[64] Patent No.: 4,518,430
Issued: May 21, 1985
Appl. No.: 539,740
Filed: Oct. 6, 1983

U.S. Applications:

[63] Continuation-in-part of Ser. No. 373,157, Apr. 29, 1982, abandoned.

[51] Int. Cl.[5] ..... C01B 25/32; C09K 3/00

[52] U.S. Cl. ..... 423/308; 106/35; 106/38.3; 106/85; 423/311; 433/199.1; 433/201.1; 433/212.1; 433/215; 433/226; 433/228.1; 501/1; 623/16

[58] Field of Search ..... 106/35, 38.3, 85; 423/308, 311; 433/199.1, 201.1, 212.1, 226, 228.1, 215; 623/16 A, 16 B; 128/92 R, 92 YQ; 501/1

[56] References Cited

U.S. PATENT DOCUMENTS

| | | | |
|---|---|---|---|
| 3,679,360 | 7/1972 | Rubin . | |
| 3,787,900 | 1/1974 | McGee | 106/35 |
| 3,913,229 | 10/1975 | Driskell . | |
| 3,929,971 | 12/1975 | Roy | 423/308 |
| 4,097,935 | 7/1978 | Jarcho . | |
| 4,497,075 | 2/1985 | Niwa et al. | 423/308 |
| 4,599,085 | 7/1986 | Riess et al. | 623/16 |

FOREIGN PATENT DOCUMENTS

| | | |
|---|---|---|
| 2008010 | 10/1979 | Fed. Rep. of Germany . |
| 58-58041 | 4/1983 | Japan . |

OTHER PUBLICATIONS

Briner et al., "Significance of Enamel Remineralization," J. Dent. Res. 11 (Supp. 1): 59–84 (1974).

Silverstone, "Remineralization Phenomena," Caries Res. 11 (Supp. 1): 59–84 (1977).

Gelhard et al., "Rehardening of Artificial Enamel Lesions in Vvvo," Caries Res. 13: 80–83 (1979).

Hiatt et al., "Root Preparation I. Obturation of Dentinal Tubules in Treatment of Root Hyper-sensitivity," J. Periodontal. 43: 373–380 (1972).

Zimmerman et al., "The Effect of Remineralization Fluids on Carious Lesions in vitro," IADR Abstract No. 282 (1979).

Levine, "Remineralisation of Natural Carious Lesions of Enamel in vitro," Brit. Dent. J., 137: 132–134 (1974).

*Guide to Dental Materials and Devices*, 7th Ed. (ADA 1974), pp. 49–66.

Driskell et al., "Development of Ceramic and Ceramic Composite Devices for Maxillofacial Application," J. Biomed. Mat. Res. 6: 345–361 (1972).

(List continued on next page.)

*Primary Examiner*—Paul Lieberman
*Assistant Examiner*—Linda D. Skaling
*Attorney, Agent, or Firm*—Allegretti & Witcoff, Ltd.

[57] ABSTRACT

Compositions that are useful and unique as dental remineralizers and dental cements, as well as methods for their use, are disclosed. The compositions are mixtures of at least two sparingly soluble calcium phosphates that are present in excess and a dilute aqueous solution approximately saturated with respect to the calcium phosphates such that they are both in near equilibrium with the saturated solution. The saturated solution is also supersaturated with respect to hydroxyapatite. Therefore, this basic constituent of dental enamel is continuously precipitated from the saturated solution and is available for the remineralization of caries lesions. The combinations of calcium phosphates containing $Ca_4(PO_4)_2O$ may also harden into dental cements that are particularly useful where contact with living tissue is required.

18 Claims, 1 Drawing Sheet

OTHER PUBLICATIONS

Brown and Chow, "Singular Points in the Chemistry of Teeth," IADR Abstract No. 120 (1975).

Gregory et al., "Solubility of $CaHPO_4.2H_2O$ in the System $Ca(OH)_2$—$H_3PO_4$—$H_2O$ at 5, 15, 25, and 37.5[C.," J. Res. Nat. Bur. Stand. 74A: 461–475 (1970).

McDowell et al., "Solubility Study of Calcium Hydrogen Phosphate. Ion Pair Formation," Inorg. Chem. 10: 1638–1643 (1971).

Gregory et al., "Solubility of —$Ca_3(PO_4)_2$ in the System $Ca(OH)_2$—$H_3PO_4$—$H_2O$ at 5, 15, 25 and 37[C," J. Res. Nat. Bur. Stand. 78A: 667–674 (1974).

McDowell et al., "Solubility of $Ca_5(PO_4)_3OH$ in the System $Ca(OH)_2$—$H_3PO_4$—$H_2O$ at 5, 15, 25 and 37.5[C," J. Res. Nat. Bur. Stand. 81A: 273–281 (1977).

Moreno et al., "Stability of Dicalcium Phosphate Dihydrate in Aqueous Solutions and Solubility of Octacalcium Phosphate," Soil Sci. Soc. Am. Proc. 21: 99–102 (1960).

Brown, "Solubilities of Phosphates and Other Sparingly Soluble Compounds," from Griffith et al., *Environmental Phosphorous Handbook* (John Wiley & Sons, New York 1973).

Brown et al., "Crystallography of Tetracalcium Phosphate," J. Res. Nat. Bur. Stands. 69A: 547–551 (1965).

Patel et al., "Solubility of $CaHPO_4.2H_2O$ in the Quaternary System $Ca(OH)_2$—$H_3PO_4$—NaCl—$H_2O$ at 25[C," J. Rest. Nat. Bur. Stands. 78A: 675–681 (1974).

LeGeros et al., "Apatitic Calcium Phosphates: Possible Dental Restorative Materials," IADR Abstract No. 1482 (1982).

Pickel et al., "The Effect of a Chewing Gum Containing Dicalcium Phosphate on Salivary Calcium and Phosphate," Ala J. Med. Sci. 2: 286–287 (1965).

SOLUBILITY PHASE DIAGRAM
FOR THE SYSTEM
$Ca(OH)_2$ - $H_2PO_4$ - $H_2O$ at 25°C
$Ca_4(PO_4)_2O$
$CaHPO_4 \cdot 2H_2O$
$CaHPO_4$
$Ca_2H_2(PO_4)_6 \cdot 5H_2O$
$\beta$-$Ca_3(PO_4)_2$
$Ca_5(PO_4)_3OH$
Solubility Isotherms at 25° C
Total Calcium - moles per liter
pH
$10^{-2}$
$10^{-3}$
$10^{-4}$
$10^{-5}$
3
4
5
6
7
8
9
10

DENTAL RESTORATIVE CEMENT PASTES

Matter enclosed in heavy brackets [ ] appears in the original patent but forms no part of this reissue specification; matter printed in italics indicates the additions made by reissue.

The invention described herein was made in the course of research partially supported by a grant from the National Institute of Dental Research.

BACKGROUND OF THE INVENTION

1. Field of the Invention

This application is a continuation-in-part of the copending application, Ser. No. 373,157, filed on Apr. 29, 1982 *now abandoned.*

This invention relates to certain combinations of sparingly soluble calcium phosphates that are unique in their application as remineralizers of caries lesions in dental enamel and partially demineralized dentin and cementum and in their application as dental cements. When used as a remineralizer the present invention not only prevents tooth decay, but can also restore the lesions caused by dental caries. The dental cements of the present invention have a variety of dental applications, but are most useful where contact between the cement and living tissue is required.

BACKGROUND OF THE INVENTION

When an incipient lesion or cavity develops on the surface of a tooth, the dentist traditionally fills the cavity that forms. This procedure may prevent the decay from spreading further, but does not restore the tooth to its original state. A considerable amount of research, however, has recently been directed to the remineralization of incipient dental lesions. The object of remineralization is to deposit $Ca_5(PO_4)_3OH$, known as hydroxyapatite, on the caries lesion such that the dental enamel incorporates the hydroxyapatite into its structure at the point of lesion. (Tooth and bone minerals are impure forms of hydroxyapatite.) Thus, remineralization prevents further tooth decay and restores the tooth.

Remineralization of tooth enamel has been carried out experimentally both in vivo and in vitro. These studies have concentrated on the remineralizing properties of saliva and synthetic solutions supersaturated with respect to hydroxyapatite. Two recent articles that give a good overview of this research are Briner et al, "Significance of Enamel Remineralization," J. Dent. Res. 53: 239–243 (1974); and Silverstone, "Remineralization Phenomena," Caries Res. II (Supp. 1): 59–84 (1977). Additional experimental work in the areas of remineralization of calcium phosphate biomaterials may be found in Gelhard et al, "Rehardening of Artificial Enamel Lesions in vivo," Caries Res. 13: 80–83 (1979); Hiatt et al, "Root Preparation I. Obduration of Dentinal Tubles in Treatment of Root Hypersensitivity," J. Periodontal. 43: 373–380 (1972); LeGeros et al, "Apatitic Calcium Phosphates: Possible Dental Restorative Materials," IADR Abstract No. 1482 (1982); Pickel et al, "The Effect of a Chewing Gum Containing Dicalcium Phosphate on Salivary Calcium and Phosphate," Ala. J. Med. Sci. 2: 286–287 (1965); Zimmerman et al, "The Effect of Remineralization Fluids on Carious Lesions in vitro," IADR Abstract No. 282 (1979); and U.S. Pat. Nos. 3,679,360 (Rubin) and 4,097,935 (Jarcho).

Generally, the supersaturated solutions or slurries used for remineralization experiments have been prepared from a single form of calcium phosphate. When a caries lesion is flooded with one of these supersaturated solutions, the calcium and phosphate ions in the form of precipitated hydroxyapatite remineralize the lesion. However, these solutions are impractical for use on patients for several reasons. First, the amount of calcium and phosphate ions available for remineralization in these supersaturated solutions is too low. It takes approximately 10,000 unit volumes of the usual supersaturated solution to product one unit volume of mineral. Thus, remineralization by this method requires both an excessive volume of fluid and an excessive number of applications. The supersaturated solutions are inherently limited in this respect because they cannot maintain their supersaturated state. When the hydroxyapatite precipitates out to the point where the solution is no longer supersaturated, new supersaturated solution must be introduced or the remineralization process stops.

An example of another kind of problem is described in Levine, "Remineralisation of Natural Carious Lesions of Enamel in vitro," Brit. Dent. J., 137: 132–134 (1974), where a phosphate buffer solution saturated with respect to $CaHPO_4.2H_2O$ (dicalcium phosphate dihydrate or brushite) and containing some fluoride was applied to dental enamel. To effect complete mineralization, exposure to the solution for three minutes every hour for 24 hours was necessary. Though the article suggested that this exposure could be achieved by use of two minute mouth rinses twice daily over the course of a year, this was admitted by the author to be an impractical procedure.

Another problem with single calcium phosphate slurries is that as the hydroxyapatite precipitates out of solution, the pH of the solution changes. Unless the old solution is removed from contact with the tooth material, the solution may become too acidic or alkaline and damage the dental tissue.

Another problem with known remineralization techniques is that the remineralization may stop before the lesion is completely remineralized due to build up of the remineralized tooth material in or on the outer layer of the tooth's surface. This build up occurs when the rate of remineralization is too fast and prevents the diffusion of the mineral into the deeper regions of the lesion, thus thwarting the full remineralization of the tooth.

There is a need for a method of remineralizing dental enamel that does not require excessive amounts of solution and inordinately long or frequent exposure times. Furthermore there is a need for a remineralization solution or slurry that can maintain a relatively constant pH and remain in a supersaturated state so that hydroxyapatite may be precipitated for a substantial period of time.

In the area of dental cements, the prior art shows an array of compounds. Some cements, however, irritate the pulp and are unsuitable for applications where the cement must come in contact with exposed pulp. Guide to Dental Materials and Devices, 7th Ed. (ADA 1974) p. 49. One solution to this problem is a cement made of materials similar in composition to tooth and bone mineral, since this would not irritate the living tissue.

The use of $\beta$-$Ca_3(PO_4)_2$ was suggested for pulp capping in Driskell et al, "Development of Ceramic and Ceramic Composite Devices for Maxillofacial Application," J. Biomed. Mat. Res. 6: 345–361 (1972); and the use of $Ca_4(PO_4)_2O$ was suggested by the inventors in IADR Abstract No. 120, J. Dent. Res. 54: 74 (1975) as a possible pulp capping agent. As described in the latter, $Ca_4(PO_4)_2O$ hydrolyzes to hydroxyapatite. Therefore, use of a calcium phosphate dental cement should provide a non-irritating cement capable of setting to a hard consistency and, when desired, remineralizing the dental tissue it contacts. Such a cement would be of great benefit, for example, as a root canal or root surface cement.

Single calcium phosphate cements, are incapable of setting to a hard consistency, however, and would suffer from the same drawbacks described above for single calcium phosphate remineralizers. They cannot maintain a relatively constant pH and do not have sufficient remineralization capacity. Though U.S. Pat. No. 3,913,229 (Driskell et al.) discloses putty-like pastes containing $\alpha$-$Ca_3(PO_4)_2$,$\beta$-$Ca_3(PO_4)_2$, $CaHPO_4$ and mixtures thereof as pulp capping, root canal, and tooth replanting materials, it is believed that none of these pastes harden into cements. Furthermore, no remineralization properties are disclosed. Thus, there is a need for a dental cement that is non-irritating, yet has good remineralizing capacity coupled with a stable pH.

SUMMARY OF THE INVENTION

The potential for application of dental remineralization is vast. Approximately $5\times10^8$ cavities are filled each year. If these half billion caries lesions were remineralized rather than being filled as cavities, the general dental health would be increased substantially, since remineralization results in a whole tooth. The present invention seeks to provide remineralization compositions and methods that can be practically applied under a dentist's care and thereby replace the need for filling of cavities.

Briefly, the present invention relates to compositions for remineralizing caries lesions. The invention concerns a combination of $Ca_4(PO_4)_2O$ (tetracalcium phosphate) and at least one other sparingly soluble calcium phosphate solid in equilibrium or quasi equilibrium with a dilute aqueous solution such that both calcium phosphates are present in excess and form a slurry. The other calcium phosphates that may be used are $CaHPO_4.2H_2O$ (dicalcium phosphate dihydrate or brushite), $CaHPO_4$ (monetite), $Ca_8H_2(PO_4)_6.5H_2O$ (octacalcium phosphate), $\alpha$-$Ca_3(PO_4)_2$,$\beta$-$Ca_3(PO_4)_2$ (tricalcium phosphates), and tricalcium phosphates modified by the addition of protons or up to approximately 10% magnesium by weight (whitlockite). All combinations of these calcium phosphates can precipitate hydroxyapatite according to the present invention. To do so, however, the two calcium phosphates must be in near equilibrium with the same saturated solution; furthermore, the saturated solution just be supersaturated with respect to hydroxyapatite. If these conditions are met, the above combinations of calcium phosphates will react to form hydroxyapatite. Since the two calcium phosphates are present in excess, the solution will remain supersaturated with respect to hydroxyapatite and will continue to precipitate this basic constituent of tooth and bone.

The advantages of a combination of calcium phosphates according to the present invention as compared with solutions or slurries of a single calcium phosphate are many. Most importantly, the inventive combination of calcium phosphates in a slurry will remain supersaturated with respect to hydroxyapatite for a significant period of time. For example, a combination of tetracalcium phosphate and brushite can remain active as a remineralizer for as long as a week. Thus, a single application of this inventive slurry to a caries lesion would suffice for complete remineralization of the afflicted area. This obviates the need for repeated and lengthy exposures required by previously proposed remineralization systems.

Another significant advantage of the present invention is that the combination of sparingly soluble calcium phosphates stabilizes the pH of the system near the point of equilibrium. This prevents wide swings in pH that might injure the dental enamel or other tissue. A stable pH also permits hydroxyapatite to continue precipitating, since hydroxyapatite will not precipitate at a low pH. Furthermore, the pH of the singular point may be altered by the addition of calcium or phosphate containing compounds to the slurry. This allows the dentist to select the most beneficial pH for remineralization.

Another advantage of the present invention is that the rate of mineralization may be adjusted to the needs of the particular lesion. The addition of simple fuoride compounds will increase the rate of mineralization. Conversely, high molecular weight crystal growth inhibitors may be added to slow mineralization. These latter compounds facilitate the remineralization of the subsurface of a caries lesion by inhibiting the remineralization of the outside surface of the tooth. This allows the hydroxyapatite ions to diffuse into the lesion's subsurface and completely remineralize the cavity.

Thus, the present invention provides compositions for the remineralization of caries lesions that are practical for clinical use due to their large remineralization capacities and stable pH's. The rate and depth of remineralization may be selected by the dentist, thereby giving substantial flexiblity to the remineralization process.

The present invention also concerns compounds useful as dental cements. The same combinations of calcium phosphates described above may be combined in a paste, rather than a slurry, and allowed to harden. The resulting cements are similar in composition to tooth and bone material and, therefore, are fully compatible with dental tissue. Though the cements of the present invention may be used in any application for which conventional dental cements are suitable, the cements of the present invention are particularly helpful where contact with living tissue is required. In addition, these cements provide the unique combination of remineralizing properties and hardening characteristics that would be especially desirable for a root canal or root surface cement because they are compatible with, protect and remineralize the sensitive surfaces of exposed roots.

Further objects and features of the invention will become apparent from the following description of the preferred embodiments and claims.

DESCRIPTION OF THE PREFERRED EMBODIMENTS

Figure 1:
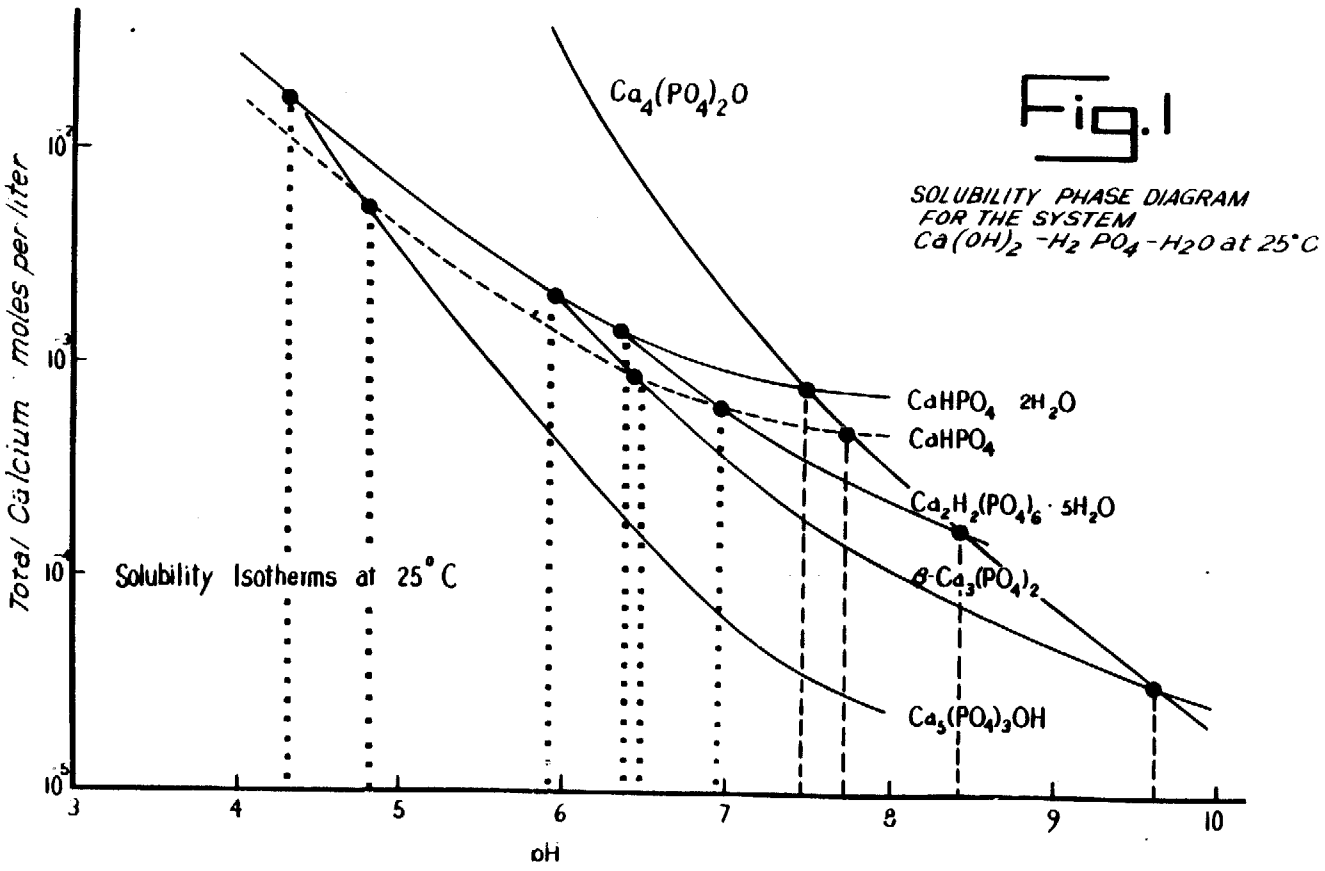
FIG. 1 is a plot of the solubility isotherms of $Ca_4(PO_4)_2O$; $CaHPO_4.2H_2O$; $CaHPO_4$; $Ca_8H_2(PO_4)_6.5H_2O$; $\beta$-$Ca_3(PO_4)_2$; and $Ca_5(PO_4)_3OH$ at 25° C. in the ternary system of $Ca(OH)_2$; $H_3PO_4$; and $H_2O$.

The sparingly soluble calcium phosphates that are relatively stable at ambient temperatures and are, therefore, available for use in the inventive remineralizing slurries and cements include $CaHPO_4.2H_2O$; $CaHPO_4$; $Ca_8H_2(PO_4)_6.5H_2O$; $\alpha$-$Ca_3(PO_4)_2$; $\beta$-$Ca_3(PO_4)_2$; tricalcium phosphates modified by protons or up to approximately 10% magnesium by weight; and $Ca_4(PO_4)_2O$. Each of these calcium phosphates has a characteristic solubility behavior that may be represented by a plot of the total concentration of calcium ions at the point of saturation versus the pH of the solution at a constant temperature. (A plot of the total concentration of phosphate ions versus pH would be equivalent for the purposes of the present invention because the concentrations of phosphate and calcium ions in solution are linked.) The resulting curve is called an isotherm.

When the isotherms for various calcium phosphates are plotted on the same axes, their solubility behavior relative to each other may be determined. Specifically, a calcium phosphate whose isotherm lies above the isotherm of another calcium phosphate at a given pH is metastable with respect to the latter. The point where the isotherms of two calcium phosphates intersect is known as a singular point. In a solution that is saturated with respect to the two calcium phosphates, both calcium phosphates will be in equilibrium with the saturated solution at the singular point. This means that neither calcium phosphate will precipitate out of solution, but another calcium phosphate whose isotherm lies below the singular point can precipitate. The present invention relates to combinations of calcium phosphates that form singular point solutions that are supersaturated with respect to hydroxyapatite.

FIG. 1 is a plot of the solubility isotherms for six calcium phosphates in the ternary system comprising $Ca(OH)_2$, $H_3PO_4$ and $H_2O$ at 25° C. The y-axis of FIG. 1 represents the total concentration of calcium ions in solution in moles per liter, while the x-axis represents pH. The isotherms for $CaHPO_4.2H_2O$, $CaHPO_4$, $\beta$-$Ca_3(PO_4)_2$ and $Ca_5(PO_4)_3OH$ are based, respectively, on the following articles: Gregory et al, "Solubility of $CaHPO_4.2H_2O$ in the System $Ca(OH)_2$-$H_3PO_4$-$H_2O$ at 5°, 15°, 25°, and 37.5° C.," J. Res. Nat. Bur. Stand. 74A: 461–475 (1970); McDowell et al, "Solubility Study of Calcium Hydrogen Phosphate. Ion Pair Formation," Inorg. Chem. 10: 1638–1643 (1971); Gregory et al, "Solubility of $\beta$-$Ca_3(PO_4)_2$ in the System $Ca(OH)_2$-$H_3PO_4$-$H_2O$ at 5°, 15°, 25° and 37° C.," J. Res. Nat. Bur. Stand. 78A: 667–674 (1974); and McDowell et al, "Solubility of $Ca_5(PO_4)_3OH$ in the System $Ca(OH)_2$-$H_3PO_4$-$H_2O$ at 5°, 15°, 25° and 37.5° C.," J. Res. Nat. Bur. Stand. 81A: 273–281 (1977). The isotherm for $Ca_8H_2(PO_4)_6.5H_2O$ is based on the solubility product disclosed in Moreno et al, "Stability of Dicalcium Phosphate Dihydrate in Aqueous Solutions and Solubility of Octacalcium Phosphate," Soil Sci. Soc. Am. Proc. 21: 99–102 (1960), while the isotherm of $Ca_4(PO_4)_2O$ is based on the approximate value of the solubility product calculated by the inventors.

As can be seen from FIG. 1, not all combinations of calcium phosphates have singular points. For example, the isotherms of $CaHPO_4.2H_2O$ and $CaHPO_4$ never cross at ambient temperature. Therefore, this pair of calcium phosphates does not embody the inventive concept of combinations of calcium phosphates that may each be in equilibrium with the same saturated solution at their singular point.

There are two additional considerations that limit the choice of calcium phosphates for the present invention. First, the singular point of the two calcium phosphates must lie above the isotherm for hydroxyapatite. This insures that a solution that is saturated with respect to the two calcium phosphates at their singular point will also be supersaturated with respect to hydroxyapatite. Thus, hydroxyapatite can precipitate out of the solution and be available for remineralization. Second, the singular point for the pair of calcium phosphates should preferably not lie too far above the isotherm for $CaHPO_4.2H_2O$, since the singular point of such a combination might be too unstable for use as a remineralizer or cement. Therefore, although $\beta$-$Ca_3(PO_4)_2$ and $Ca_8H_2(PO_4)_6.5H_2O$ have intersecting isotherms, their singular point lies far above the isotherm for $CaHPO_4.2H_2O$ and is probably unsuitable.

The circles in FIG. 1 define singular point compositions for the various pairs of solids in solution. As can be seen from FIG. 1, the following combinations of calcium phosphates are definitely available as remineralizers and cements according to the present invention: $CaHPO_4.2H_2O$ with $\beta$-$Ca_3(PO_4)_2$, $Ca_8H_2(PO_4)_6.5H_2O$, or $Ca_4(PO_4)_2O$; $CaHPO_4$ with $\beta$-$Ca_3(PO_4)_2$, $Ca_8H_2(PO_4)_6.5H_2O$, or $Ca_4(PO_4)_2O$; and $Ca_4(PO_4)_2O$ with $Ca_8H_2(PO_4)_6.5H_2O$ or $\beta$-$Ca_3(PO_4)_2$. Additionally, there are potentially three or four singular point compositions containing $\alpha$-$Ca_3(PO_4)_2$. Likewise, the isotherms of the modified tricalcium phosphates may define additional inventive compositions.

The reason that a singular point composition has such desirable properties as a remineralizer and cement is that it resists changes in the pH or composition of the solution by driving itself back to the singular point whenever the composition or pH changes. For example, if two calcium phosphates that possess a singular point were present in excess in a solution that was more acidic than the pH of the singular point, the more basic phosphate would dissolve and cause the more acidic phosphate to precipitate. This process would continue until the pH and the composition were forced back to the singular point, where the two calcium phosphates present in excess would both be in equilibrium with the solution and neither would precipitate out of solution. The reverse process would occur if the composition started at a point more basic than the singular point pH.

When only two salts are present in the solution, the composition of the solution cannot rise above the isotherm of the more soluble salt or fall below the isotherm of the less soluble salt. Furthermore, the solution will only be in equilibrium at the singular point. However, the precipitation of a third salt, such as hydroxyapatite, may drive the composition in the direction of the third salt's isotherm. The degree of deviation depends upon the relative rates of dissolution and precipitation of the three salts.

For the purposes of remineralization, it would be undesirable if the solution's composition deviated too close to the isotherm of hydroxyapatite since this would lower the rate of precipitation of hydroxyapatite. However, since the two calcium phosphates are present in excess, the relative rate of precipitation for hydroxyapatite is likely to be small when compared to the dissolution and precipitation rates of the other two calcium phosphates, and the composition will remain in the vicinity of the singular point. Thus, a slurry containing excessive amounts of two calcium phosphates having a singular point can remain approximately at the pH and composition of the singular point despite the constant production and precipitation of hydroxyapatite. It is this feature of the present invention that permits a remineralizing slurry or paste to remain active as a remineralizer for a substantial period of time without great shifts in pH or composition.

The combinations of calcium phosphates listed above that have singular points all react to form hydroxyapatite. However, these combinations fall into two distinct classes: those containing $Ca_4(PO_4)_2O$ and those that do not. $Ca_4(PO_4)_2O$ is the most basic calcium phosphate of the present invention. Therefore, any of the remaining calcium phosphates that are more acidic than hydroxyapatite can react directly with tetracalcium phosphate to form hydroxyapatite. For example, $$Ca_4(PO_4)_2O + CaHPO_4.2H_2O = Ca_5(PO_4)_3OH + 2H_2O;$$

$$Ca_4(PO_4)_2O + CaHPO_4 = Ca_5(PO_4)_3OH;$$

$$3Ca_4(PO_4)_2O + Ca_8H_2(PO_4)_6.5H_2O = 4Ca_5(PO_4)_3OH + 4H_2O; \text{ and}$$

$$Ca_4(PO_4)_2O + 2Ca_3(PO_4)_2[\alpha,\beta, \text{ or modified}] + H_2O = 2Ca_5(PO_4)_3OH.$$

However, when both salts are more acidic than hydroxyapatite, the more acidic salt is a reaction product along with hydroxyapatite. Thus, $$2Ca_3(PO_4)_2[\alpha,\beta, \text{ or modified}] + 3H_2O = Ca_5(PO_4)_3OH + CaHPO_4.2H_2O;$$

$$2Ca_3(PO_4)_2[\alpha,\beta, \text{ or modified}] + H_2O = Ca_5(PO_4)_3OH + CaHPO_4;$$

$$Ca_8H_2(PO_4)_6.5H_2O + 2H_2O = Ca_5(PO_4)_3OH + 3CaHPO_4.2H_2O; \text{ and}$$

$$Ca_8H_2(PO_4)_6.5H_2O = Ca_5(PO_4)_3OH + 3CaHPO_4.$$

In such cases, the more acidic salt provides a template that removes the acidic phosphate ions by crystallizing the acid salt. The removal of the acidic ions holds the pH of the solution near the singular point and maintains the supersaturated state of the solution with respect to hydroxyapatite that is necessary for remineralization. However, these latter reactions are not as advantageous as the combinations including $Ca_4(PO_4)_2O$ since one of the calcium phosphates must serve as reaction product. This is less efficient in producing $Ca_5(PO_4)_3OH$ than the $Ca_4(PO_4)_2O$ containing compositions. Additionally, the more acidic calcium phosphates that serve as reaction products are not removed from the slurry as the remineralization progresses. Therefore, these combinations are more detrimental to living tissue than are the $Ca_4(PO_4)_2O$ containing combinations.

The reaction approximated by $5Ca_8H_2(PO_4)_6.5H_2O = 8Ca_5(PO_4)_3OH + 6H_3PO_4 + 17H_2O$, is of particular interest for remineralization, because under many conditions the rate of formation of octacalcium phosphate appears to be much greater than the rate of formation of hydroxyapatite. Since octacalcium phosphate can hydrolyze in situ to hydroxyapatite, the formation of $Ca_8H_2(PO_4)_6.5H_2O$ followed by hydrolysis to hydroxyapatite may be a particularly efficacious method for the production of hydroxyapatite in remineralizing solutions. The only known combinations of calcium phosphates that definitely can form octacalcium phosphate as a precursor to hydroxyapatite are $Ca_4(PO_4)_2O$ with $CaHPO_4.2H_2O$ and $CaHPO_4$ since their singular points both lie above the isotherm for $Ca_8H_2(PO_4)_6.5H_2O$. However, the singular points of $\alpha$-$Ca_3(PO_4)_2$ with $CaHPO_4.2H_2O$ and $CaHPO_4$ might also form octacalcium phosphate as a precursor to hydroxyapatite.

The pH range of the inventive system may be predetermined by choosing a pair of calcium phosphates with an appropriate singular point pH. For example, if a pH around 7.5 is desired, one could use the combination of $CaHPO_4.2H_2O$ and $Ca_4(PO_4)_2O$. The pH of any slurry or paste may be further altered by the addition of up to approximately 10% by weight of simple calcium or phosphate containing compounds. These compounds change the pH of the singular point by altering the Ca/P ratio of the solution. Since the chemical potentials of $Ca(OH)_2$ and $H_3PO_4$ have been shown to be invariant in the presence of additional components at a given singular point [See Brown, "Solubilities of Phosphates and Other Sparingly Soluble Compounds," from Griffith et al, Environmental Phosphorous Handbook (John Wiley & Sons, New York 1973)], the ratio $(Ca^{2+})/(H^+)^2$ is constant at a given singular point, where the parentheses denote ion activities. Thus, the addition of an acidic compound, such as HCl, $CaCl_2$, or $Ca(C_2H_3O_2)_2$, will increase the ionic activity of $Ca^{2+}$, increase the Ca/P ratio of the singular point and cause the singular point to move to a lower pH. Similar considerations hold for the addition of basic compounds. Examples of suitable base and phosphate containing compounds are $NaH_2PO_4$ and $(NH_4)H_2PO_4$.

The rate of remineralization may also be adjusted. The addition of simple or complex fluoride compounds such that the fluoride content of the slurry or paste is up to approximately 3.8% by weight will increase the rate of precipitation of hydroxyapatite and decrease solubility, thereby providing a control on the body's ability to resorb the material. Examples of possible fluoride additives are $CaF_2$, $SrF_2$, NaF, $Na_2SiF_6$, and $Na_2PO_3F$. Through rapid mineralization is beneficial under some circumstances, it may cause the remineralization of the outside surface of an incipient caries lesion and prevent the remineralization of the subsurface region of the lesion. A moderately slow remineralization rate would allow all parts of the lesion to be healed. The particular calcium phosphates used will affect the rate of remineralization. In addition, particle size is a factor since as particle size increases, the rate of mineralization decreases. Generally the particle size for remineralization slurries should be greater than 5 $\mu$m. Thus, to remineralize a deep lesion, a slow remineralizing slurry could be applied to the tooth by means of a bite block sponge, periodontal pack, cement or rigid gel.

It is also possible to facilitate internal remineralization by etching the surface of the tooth such that the remineralizing slurry can contact more of the lesion's surface at once. Another solution to the problem of incomplete internal remineralization is the application of high molecular weight crystal growth poisons or inhibitors onto the tooth surface. Examples of such growth inhibitors are proteoglycans, glycoproteins, polylysine, and protamine. Concentrations of up to approximately 5% by weight may be added to the remineralizing slurry. These inhibitors prevent the growth of hydroxyapatite crystals at the surface of the tooth but do not tend to diffuse into the interior of the tooth. Accordingly, they inhibit the remineralization of the caries lesion's surface and prevent the blockage of the channels necessary for the diffusion of calcium and phosphate ions into the subsurface lesion.

All of the combinations of calcium phosphates described above containing $Ca_4(PO_4)_2O$ may be used as dental cements. The two main differences between the inventive remineralizers and the inventive cements are particle size and solid-to-liquid ratio. For use as cements, the selected calcium phosphates should be ground to a finer particle size, preferably less than 5 μm. Additionally, calcium phosphate particles are combined with much less solution so that a paste is formed rather than a slurry. The paste then hardens to a bonelike consistency.

Porous cements that are especially useful as bone implants or protheses may be prepared by combining the calcium phosphates with a highly water soluble material, such as granular sugar, and subjecting this mixture to pressure sufficient to form a compact mass. The water necessary for the inventive reaction is usually contained in the calcium phosphates themselves. However, a small amount of water may be added to the mixture before pressure is applied in order to facilitate the setting of the cement. The resulting mass is then placed into hot water such that the highly water soluble material is removed. A porous cement remains that is readily permeated by organic bone tissue.

The cements of the present invention may be used in place of any of the cements known in the prior art as: (i) cavity bases and liners to protect the pulp, (ii) materials for capping exposed pulps, (iii) materials to replace or promote regeneration of bone mineral lost due to periodontal disease, (iv) direct filling materials that have physical properties similar to enamel and are adhesiveto enamel and dentin, (v) a cement to build up alveolar ridges in edentulous patients, (vi) an endodontic filling material for root canals, (vii) a material to cement retention pins, (viii) a material for filling sockets after a tooth extraction, (ix) a replacement of bone that has been removed surgically or lost due to trauma, (x) a cement for implanting or replanting teeth, (xi) a luting cement in dentistry and orthopaedic surgery, (xii) an investment mold material, (xiii) a material which will promote bone mineral growth in its vicinity, (xiv) a remineralizing polish for use in place of pumice, and (xv) a root cement for remineralizing and desensitizing of exposed root surfaces. Since the inventive cements are fully compatible with living tissue, they are especially advantageous where contact with dental tissue is necessary. In addition, the cements possess remineralization capabilities. Thus, the discussion above with respect to the use of the inventive compositions as remineralizers is fully applicable to their use as cements.

The strength and hardness of the present cements can be controlled by the particle size of the calcium phosphates, the presence of hydroxyapatite or $Ca_5(PO_4)_3F$ (fluorapatite) as seed or matrix crystals, and by the use of crystal habit modifiers. These last compounds promote the growth of more needle-like apatitic crystals in the cement. It is believed that a particle size of 1 μm would result in a very strong cement.

The setting time of the present cements may be reduced by adding a sizable amount of hydroxyapatite or fluorapatite seed crystals to the paste as these compounds facilitate crystal formation. This may also increase the hardness of the cement and minimize shrinkage or expansion during set. Of course, it may be desirable to have some setting expansion when the paste is used in a cavity preparation in order to promote adhesion to the cavity wall. Such expansion may be achieved by the addition of $\beta$-$Ca_3(PO_4)_2$ or up to 1% by weight of crystal habit modifiers, such as $Mg^{2+}$, $Sr^{2+}$, citrate, phosphonates, carbonate, polyphosphates, sucrose phosphate and phosphocitrate. These modifiers absorb onto the specific sites of the crystal surfaces during growth, thereby affecting the morphology of the crystals. Additionally, appropriate combinations of varying or "gap-graded" particle sizes would promote setting expansion.

It has also been determined that when fluoride compounds are added to the liquid or solid phase, the setting time may be reduced further for the same seed crystal content.

EXAMPLE 1

Two calcium phosphates having a singular point with an appropriate pH are selected. Their singular point should not lie too far above the isotherm for $CaHPO_4.2H_2O$ and must lie above the isotherm for hydroxyapatite. The calcium phosphates selected may be prepared by the methods described in McDowell et al, "Solubility Study of Calcium Hydrogen Phosphate. Ion-Pair Formation," Inorg. Chem. 10: 1638–1643 (1971); Gregory et al, "Solubility of $\beta$-$Ca_3(PO_4)_2$ in the System $Ca(OH_2)$-$H_3PO_4$-$H_2O$ at 5°, 15°, 25° and 37° C.," J. Res. Nat. Bur. Stand. 78A: 667–674 (1974); Moreno et al, "Stability of Dicalcium Phosphate Dihydrate in Aqueous Solutions and Solubility of Octacalcium Phosphate," Soil Sci. Soc. Am. Proc. 21: 99–102 (1960); Brown et al, "Crystallography of Tetracalcium Phosphate." J. Res. Nat. Bur. Stands. 69A: 547–551 (1965); and Patel et al, "Solubility of $CaHPO_4.2H_2O$ in the Quaternary System $Ca(OH)_2$-$H_3PO_4$NaCl-$H_2O$ at 25° C.," J. Rest. Nat. Bur. Stands. 78A: 675–681 (1974). The calcium phosphates may be in crystalline, cryptocrystalline, finely divided, or amorphous form.

Each of the selected, solid calcium phosphates is then ground to the desired particle size. Generally for remineralization slurries, the particle size should be greater than 5 μm, since this size prolongs the remineralization potential of the slurry by slowing the remineralization rate. Larger particle size both slows the reaction rate and retards the setting or hardening of the slurry.

The ground calcium phosphates are then mixed in excess in a dilute aqueous solution that is either slightly acidic or slightly basic to form a slurry. Examples of appropriate acidic solutions are water and $H_3PO_4$ or HCl, whle examples of appropriate basic solutions are water and $Ca(OH)_2$ or KOH. The slurry may be applied to the affected area by means of a bite block sponge, periodontal pack, cement, or rigid gel. Also the slurry may be applied by burnishing, spatulation or packing and covering by various mechanical means. Additionally, the slurry may be allowed to harden and thereby act as its own cement for holding the remineralizer against the afflicted area.

Alternatively, the above remineralizing combinations may be incorporated into chewing gum formulations by blending the solid and liquid phases with a chewing gum base in the manner practiced in the industry. Similarly, the solid and liquid phases may be combined with the common ingredients of toothpaste. In these cases the particle size of the calcium phosphates should be such as to avoid grittiness.

In addition, three groups of compounds may be added to the liquid phase of the remineralization slury. First, fluoride compounds, such as $CaF_2$, $SrF_2$, NaF, $Na_2SiF_6$, or $Na_2PO_3F$, may be added to increase the rate of mineralization. Second, calcium and phosphate containing compounds, such as $CaCl_2$, $Ca(C_2H_3O_2)_2$, $NaH_2PO_4$, or $(NH_4)H_2PO_4$, may be added to modify the Ca/P ratio and pH of the solution'singular point. Third, high molecular weight crystal growth inhibitors may be added to facilitate the complete remineralization of the subsurface caries lesions.

EXAMPLE 2

$Ca_4(PO_4)_2O$ and $CaHPO_4.2H_2O$ are ground to an approximate mean particle size of 40 μm. Two grams of an equimolar mixture of the two solids is combined with 20 ml of a 5mM $H_3PO_4$ solution and mixed to form a slurry. The slurry is then placed on a caries lesion by means of a bite block sponge. This slurry will maintain a pH in the vicinity of 7.4 and precipitate hydroxyapatite for almost one week.

EXAMPLE 3

To form a dental cement, $Ca_4(PO_4)_2O$ and at least one other calcium phosphate selected from the group consisting of $CaHPO_4.2H_2O$, $CaHPO_4$, $Ca_8H_2(PO_4)_6.5H_2O$, α-$Ca_3(PO_4)_2$, β-$Ca_3(PO_4)_2$, and modified $Ca_3(PO_4)_2$ are ground to a uniform particle size of less than 5 μm so that the setting time will be reasonable. If some setting expansion is required, "gap-graded" particle sizes may be used. The calcium phosphates are then combined with the dilute aqueous solutions of Example 1 to form a paste. This paste is then applied by an appropriate means to the affected area. For example, if the cement is to be used as an endodontic filling material, the paste may be applied by injection or packed with a plugger.

To modify the remineralization properties of the cement, the additives described in Example 1 may be added to the liquid phase. In addition, crystal habit modifiers may be added to induce more needle-like growth of apatitic crystals. The setting time for a given cement may be reduced by adding hydroxyapatite or fluorapatite seed crystals. The inclusion of fluoride compounds will further reduce the setting time.

Setting expansion and shrinkage may be reduced by adding a sizable amount of hydroxyapatite to the paste. Conversely, some setting expansion may be encouraged by the addition of β-$Ca_3(PO_4)_2$ or crystal habit modifiers.

EXAMPLE 4

Specimens 1–5 shown in Table I were prepared as follows. The two calcium phosphates and hydroxyapatite seed were all ground to a mean particle size of 5 μm. One gram of a mixture containing equimolar amounts of the two calcium phosphates and the appropriate weight percent of $Ca_5(PO_4)_3OH$ was mixed with 0.5 ml of the appropriate $H_3PO_4$ solution. All of the specimens were stirred into pastes, allowed to harden, and were soaked in $H_2O$ at 37° C. for twenty-four hours. The compressive strengths in pounds per square inch were then determined as shown in Table I.

EXAMPLE 5

Specimens 6–9 shown in Table II were prepared by grinding $Ca_4(PO_4)_2O$, $CaHPO_4.2H_2O$, and $Ca_5(PO_4)_3OH$ to a mean particle size of 5 μm. One gram of a mixture containing equimolar amounts of $Ca_4(PO_4)_2O$ and $CaHPO_4.2H_2O$ and the appropriate weight percent of $Ca_5(PO_4)_3OH$ was mixed with 0.5 ml of 20mM $H_3PO_4$ to form a paste. This paste was then allowed to harden. The setting times as a function of apatite seed content are shown in Table II.

EXAMPLE 6

To form a porous cement of increased strength, $Ca_4(PO_4)_2O$ and $CaHPO_4.2H_2O$ are ground to a mean particle size of 5 μm. Two grams of a mixture containing equimolar amounts of the two calcium phosphates and 0.5 gram of granular sugar (or another highly water soluble material) are mixed and placed in a mold.

TABLE I

COMPRESSIVE STRENGTHS OF EXPERIMENTAL CEMENTS

| Specimen | Calcium Phosphates | $Ca_5(PO_4)_3OH$, Wt % Seed Content | Solution | Compressive Strength (PSI)[1] |
|---|---|---|---|---|
| 1 | $CaHPO_4.2H_2O$ + $Ca_4(PO_{42})O$ | 0 | 5 mM $H_3PO_4$ | 4390 ± 860 (3) |
| 2 | $CaHPO_4.2H_2O$ + $Ca_4(PO_4)_2O$ | 0 | 20 mM $H_3PO_4$ | 4560 ± 520 (3) |
| 3 | $CaHPO_4$ + $Ca_4(PO_4)_2O$ | 0 | 20 mM $H_3PO_4$ | 4960 ± 650 (3) |
| 4 | $CaHPO_4$ + $Ca_4(PO_4)_2O$ | 2.7 | 20 mM $H_3PO_4$ | 4280 ± 940 (2) |
| 5 | $CaHPO_4$ + $Ca_4(PO_4)_2O$ | 9.6 | 20 mM $H_3PO_4$ | 4578 ± 1010 (2) |

[1]Compressive strengths are shown as mean value ± standard deviation. The number of samples is shown in parentheses.

TABLE II

SETTING TIME AS A FUNCTION OF HYDROXYAPATITIC SEED CONTENT FOR EXPERIMENTAL CEMENTS

| Specimen | $Ca_5(PO_4)_3OH$ Content, Wt % | Setting Time[1] Min. |
|---|---|---|
| 6 | 0 | 22 |
| 7 | 24 | 11 |
| 8 | 34 | 9 |
| 9 | 43 | 8 |

[1]The setting times were measured according to American Dental Association Specification No. 9.

Usually addition of water to the mixture is not needed but a small amount may be added in some instances to facilitate the setting reaction. Up to 80,000 pounds per square inch of pressure is applied to the cement mixture using a press for two minutes. The specimen, which is made into a compact mass by the process, is placed in boiling water to extract the water soluble granules and to complete the setting process. The resulting porous materials can be used as protheses which can be invaded more readily by organic bone tissue.

It should be understood that the foregoing disclosure emphasizes certain specific embodiments of the invention and that all modifications of alternatives equivalent thereto are within the spirit or scope of the invention.

We claim as our invention:

1. A [dental restorative] paste *consisting essentially of* [comprising] an aqueous mixture of $Ca_4(PO_4)O$ and at least one other calcium phosphate selected from the group consisting of $CaHPO_4.2H_2O$ [,] *and* $CaHPO_4$, [$Ca_8H_2(PO_4)_6.5H_2O$, β-$Ca_3(PO_4)_2$, β-$Ca_3(PO_4)_2$, and modified $Ca_3(PO_4)_2$, the paste being capable of hardening] *which aqueous mixture hardens* into a cement *at an ambient temperature.*

2. The paste of claim 1 wherein the other calcium phosphate is $CaHPO_4.2H_2O$.

3. The paste of claim 1 wherein the other calcium phosphate is $CaHPO_4$.

[4. The paste of claim 1 wherein the other calcium phosphate is $Ca_8H_2(PO_4)_6.5H_2O$.]

[5. The paste of claim 1 wherein the other calcium phosphate is $\beta$-$Ca_3(PO_4)_2$.]

6. The paste of claim 1 wherein both calcium phosphates are in crystalline, cryptocrystalline, or amorphous form.

7. The paste of claim 1 further [comprising] *including* up to approximately 10% by weight of additional calcium or phosphate containing compounds *in an amount sufficient to alter the pH of the paste.*

8. The paste of claim 7 wherein the additional calcium containing compounds [comprise] *are selected from the group consisting of* $CaCl_2$ [or] *and* $Ca(C_2H_3O_2)_2$.

9. The paste of claim 7 wherein the additional phosphate containing compounds [comprise] *are selected from the group consisting of* $NaH_2PO_4$ [or] *and* $(NH_4)H_2PO_4$.

10. The paste of claim 1 further [comprising] *including* fluoride containing compounds such that the fluoride content of the paste is up to approximately 3.8% by weight *in an amount sufficient to increase the rate of precipitation of hydroxyapatite from the paste.*

11. The paste of claim 10 wherein the fluoride containing compounds [comprise] *are selected from the group consisting of* $CaF_2$, $SrF_2$, NaF, $Na_2SiF_6$ [or] *and* $NaPO_3F$.

12. A paste [comprising] *consisting essentially of* $CaHPO_4$ and $Ca_4(PO_4)_2O$ having a particle size of approximately 1 $\mu$m and a 20mM solution of $H_3PO_4$, *the paste hardening into a cement at an ambient temperature.*

13. The paste of claim 1 additionally [comprising] *including* a seed crystal compound selected from the group consisting of hydroxyapatite and fluorapatite *in an amount sufficient to reduce the setting time of the cement.*

*14. The paste of claim 13 wherein the seed crystal compound is hydroxyapatite, the hydroxyapatite being present in an amount up to 43% by weight and in an amount sufficient to reduce the setting time of the cement.*

*15. The paste of claim 1 additionally including up to approximately 5% by weight of a high molecular weight crystal growth inhibitor selected from the group consisting of proteoglycans, glycoproteins, polylysine and protamine in an amount sufficient to inhibit the growth of hydroxyapatite crystals.*

*16. The paste of claim 1 additionally including* $\beta$-$Ca_3(PO_4)_2$ *in an amount sufficient to achieve setting expansion of the cement.*

*17. The paste of claim 1 additionally including up to 1% by weight of a crystal habit modifier selected from the group consisting of* $Mg^{2+}$, $Sr^{2+}$, *citrate, phosphonates, carbonate, polyphosphates, sucrose phosphate, and phosphocitrate in an amount sufficient to achieve setting expansion of the cement.*

*18. The paste of claim 1 wherein the paste is slightly acidic.*

*19. The paste of claim 1 where in the paste is slightly basic.*

*20. The paste of claim 1 additionally including granular sugar, the sugar being present in an amount up to 20% by weight and in an amount sufficient to form a porous cement upon removal of the sugar by application of hot water to the cement.*

* * * * *